United States Patent [19]
Armellino et al.

[11] Patent Number: 5,972,916
[45] Date of Patent: Oct. 26, 1999

[54] COMPOSITIONS CONTAINING THE NONPRESCRIPTION COMBINATION OF ACETAMINOPHEN, ASPIRIN AND CAFFEINE TO ALLEVIATE THE PAIN AND SYMPTOMS OF MIGRAINE

[75] Inventors: Joseph Armellino, Chester; Randy Koslo, West Windsor Township, both of N.J.

[73] Assignee: Bristol-Myers Squibb Company, New York, N.Y.

[21] Appl. No.: 09/021,284

[22] Filed: Feb. 10, 1998

Related U.S. Application Data

[60] Provisional application No. 60/052,426, Jul. 14, 1997.

[51] Int. Cl.$^6$ .......................... A61K 31/60; A61K 31/52; A61K 31/165
[52] U.S. Cl. ........................... 514/165; 514/264; 514/630
[58] Field of Search ..................................... 514/264, 165, 514/630

[56] References Cited

U.S. PATENT DOCUMENTS

| | | | |
|---|---|---|---|
| 3,080,287 | 3/1963 | Lewenstein | 167/65 |
| 4,017,614 | 4/1977 | Wild | 424/232 |
| 4,585,866 | 4/1986 | Fozard et al. | 546/129 |
| 4,758,433 | 7/1988 | Johnson et al. | 424/195.1 |
| 5,273,759 | 12/1993 | Simmons | 424/465 |
| 5,538,959 | 7/1996 | Mauskop | 514/165 |

FOREIGN PATENT DOCUMENTS

| | | |
|---|---|---|
| 19502789 A1 | 8/1996 | Germany . |
| 5504618 | 10/1978 | Japan . |
| 2034533 | 5/1995 | Russian Federation . |
| 2101014 | 1/1998 | Russian Federation . |
| 277525 | 2/1993 | Sierra Leone . |
| 9507082 | 3/1995 | WIPO . |

OTHER PUBLICATIONS

Bosse et al., Treatment of headaches of very different origin, Therapiewoche 38, 3879–3884 (1998).
Physicians' Desk Reference for nonprescription drugs, 1990, p. 530.
Rasmussen, Birthe Krogh, et al., Impact of headache on sickness, absence and utilization of medical services: a Danish population study, Journal fo Epidemiology and Community Health, 1992; 46:443–446.
Lipton, Richard B., M.D., Gallup Poll of Migraine Sufferers, Headache Newslatter, Nov. 1995, american Council for Headache Education, Woodbury, N.J. 08096.
Edmeads, John et al., Impact of Migraine and Tension–Type Headache on Life Style, Consulting Behavior, and Medication Use: A Canadian Population Survey, the Canadian Journal of Neurological Sciences, May 1993, vol. 20, No. 2, p. 131–7.
Editorial, Over–the–Counter Medication and the Treatment of Migraine, Headache 1994; 34:547–548.
Stang, Paul E., Ph.D., PA–C, et al,; Migraine: Patterns of healthcare use, Neurology, Jun. 1994, 44(Suppl4): S47–S55.
Olesen, J., A review of current drugs for migraine, J. Neurol (1991) 238:S23–S27.
Laska, Eugene M., Ph.D, et al., Caffeine as an Analgesic Adjuvant, JAMA, Apr. 6, 1984; vol. 251, No. 13, p. 1711–18.
Migliardi, Joseph R., MD., et al., Caffeien as an analgesic adjuvant in tension headache, Clinical Pharmacology & Therapeutics, vol. 56, No. 5, p. 576–86.
Rasmussen, Birthe Krogh, et al., Migraine, Epidemiology, Headaches, Chapter 22, p. 169–173, Raven Press, New York, N.Y., 1993.
Solomon, Glen D., M.D. FACP, Therapeutic Advances in Migraine, J. Clin. Pharmacol 1993; 33: 200–209.
RoteListe 1995, p. 256.
Drug Launch, 94: 15622 (Aug. 1986).
Lehmann, Horst, et al., Studies on the Chronic Oral Toxicity of an Analgesic Drug Combination Consisting of Acetylsalicylic Acid, Paracetamol and Caffeine in Rats Including an Electron Microscopical Evaluation of Kidneys, Arzneim.–Forsch./Drug Res. 46(II), 895–905(1996).
G. Haag, Elzack–Oberprechtal; Deutsche Apotheker Zeitung, 1998: pp. 229–234.
Hans–Christoph Diener, Klaus–Ulrich Bühler, Johannes Dichgans, Stefan Geiselhart, Dieter Gerber, Erich Scholz, Tübingen; Arzneimitteltherapie, vol. 6, No. 5, 1988, pp. 156–164.

*Primary Examiner*—Phyllis G. Spivack
*Attorney, Agent, or Firm*—Charles J. Zeller; Thomas R. Savitsky

[57] ABSTRACT

The invention provides a safe and economical nonprescription combination of acetaminophen, aspirin and caffeine (APAP/ASA/CAF) for use in treating migraine pain and the cluster of symptoms characteristic of migraine attack, such as nausea, photophobia, phonophobia and functional disabilities. The use of the APAP/ASA/CAF combination is also effective in aborting the prodrome phase of a migraine attack.

17 Claims, 4 Drawing Sheets

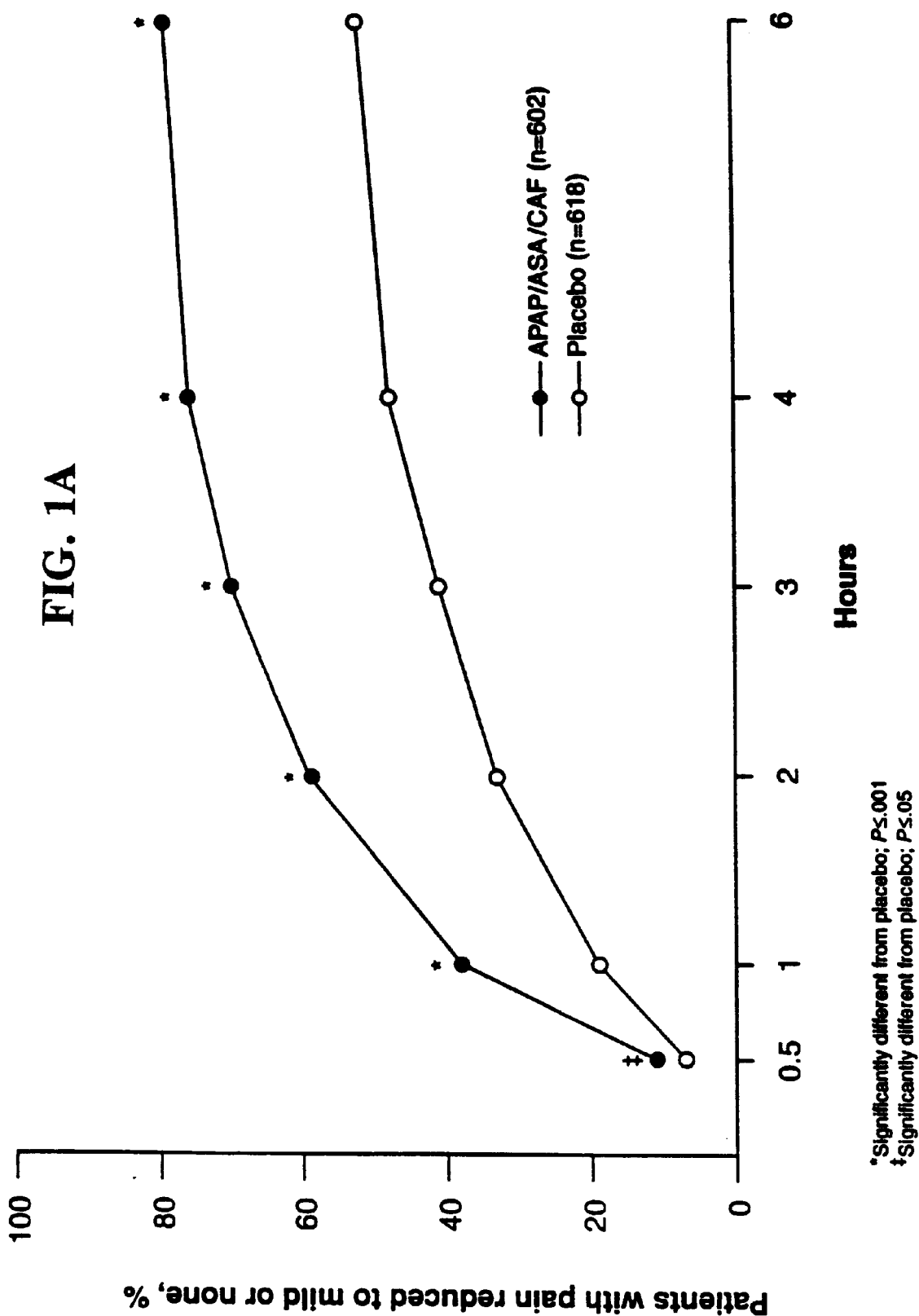

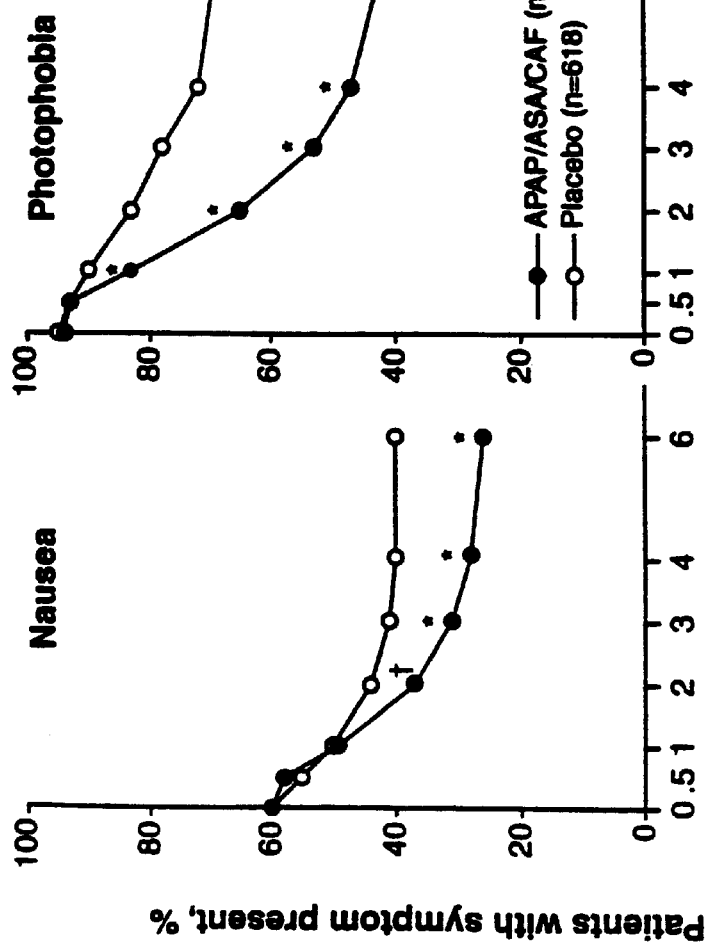

COMPOSITIONS CONTAINING THE NONPRESCRIPTION COMBINATION OF ACETAMINOPHEN, ASPIRIN AND CAFFEINE TO ALLEVIATE THE PAIN AND SYMPTOMS OF MIGRAINE

This application is a continuation of provisional No. 60/052,426 filed Jul. 14, 1997.

FIELD OF THE INVENTION

The present invention relates generally to compositions and methods used to alleviate the symptoms and pain associated with acute migraine attack. More particularly, the present invention relates to the use of a nonprescription combination of acetaminophen, aspirin and caffeine for treating individuals afflicted with pre-migraine conditions, migraine-associated symptoms and/or migraine pain of mild to severe intensity.

BACKGROUND OF THE INVENTION

An estimated 23 to 25 million Americans—about 18% of women and 6% of men—suffer from migraine pain and migraine-related symptoms[1]. Attacks are common, with more than 50% of sufferers experiencing one or more episodes per month[2].

Migraine, a heterogeneous disorder, produces a wide spectrum of pain and associated disabilities, both within and among individual sufferers. The spectrum includes mild pain and no disability in approximately 5–15% of migraine attacks, moderate to severe pain and disability in approximately 60–70% of attacks, and incapacitating pain and total disability in the remaining approximately 25–35% of attacks[3,4].

Recent population-based epidemiological studies in the United States and elsewhere, have found that most people with migraine are not currently consulting a physician for their migraine attacks, and only about one-third have ever been diagnosed by a doctor[5,6,7,8]. The overwhelming majority (95% of men and 97% of women) of migraineurs, i.e., individuals who suffer from migraines, used medication to assuage their pain, although only about 28% of the men and 40% of the women have ever used prescription medications[9,10]. More than 90% of migraineurs use nonprescription medication for their migraines and the majority use nonprescription medications exclusively[5,11].

Many migraine sufferers use single-agent nonprescription analgesics such as acetaminophen, or aspirin, or nonsteroidal anti-inflammatory agents to treat their attacks[12,13]. Despite the widespread use of nonprescription drugs for self-treatment, only prescription drugs are approved for the treatment of migraine in the United States. In other countries, a number of nonprescription drugs are specifically approved for migraine pain[13]; however, the effectiveness of self-treatment of migraine and the effectiveness of such nonprescription drugs in relieving or aborting migraine pain and/or the characteristic symptoms of migraine has not been adequately studied in well-controlled clinical trials[12,13]. Acetaminophen, aspirin and caffeine is approved for relief of nonspecific headaches and tension headaches[15], which are clinical and phsyiologically distinct from migraine. Caffeine is an analgesic adjuvant for a variety of pain conditions and has been included in combination with other analgesics, ergot alkaloids and barbiturates in prescription formulations for migraine[14,16,17,18].

Although the symptom pattern varies among migraine sufferers, the severity of migraine pain justifies a need for vigorous therapy in the great majority of cases. Traditional therapy, such as ergotamine, although effective during prodrome of migraine attack, is known to become progressively less effective if its administration is delayed. Ergotamine is frequently combined with caffeine, a known analgesic adjuvant, to facilitate absorption of the ergot alkaloid. However, repeated dosing of ergotamine induces long-lasting and cumulative vasoconstriction, thereby requiring careful instructions and management of individuals who take oral preparations for migraine attack.

Because of the cumulative toxicity of ergotamine and its derivatives, safer therapeutics for the treatment and prophylaxis of migraine have been sought. Examples of such ergotamine alternatives are ergonovine, propranolol and methysergide; however, significant toxicity also occurs in nearly 40% of the individuals who take these agents. In addition, many of these agents are completely ineffective in the treatment of acute migraine. A prescription antimigrainous medication which is an alternative to ergotamine and its derivatives is sumatriptan (or sumatriptan succinate), which is a selective 5-hydroxytryptamine$_1$ receptor subtype agonist that is effective in the prodrome phase of a migraine attack.

Thus, a clear goal in the art is to discover new, safe, nontoxic and effective anti-migraine drugs and treatments, particularly nonprescription treatment medications that can be self-administered without the need of a medical prescription.

Until the present invention, the nonprescription combination of acetaminophen, aspirin and caffeine (APAP/ASA/CAF) has not been demonstrated to be a useful treatment for the pain and the symptoms of migraine attack, which is clinically and physiologically considered to be distinct from non-migraine headaches, such as nonspecific headaches or tension headaches. In addition, prior to the present invention, the combination of acetaminophen, aspirin and caffeine (APAP/ASA/CAF) was not discovered to alleviate one or more of the symptoms of migraine, such as nausea, photophobia, phonophobia and functional disabilities. Further, prior to the present invention, the APAP/ASA/CAF combination had not been discovered to abort the prodrome phase of a migraine attack, i.e., the phase prior to migrainous aura and acute migraine pain. Moreover, not until the present invention as described herein was it discovered that a combination of APAP/ASA/CAF efficaciously aborted migraine pain and also significantly reduced the migraine symptoms of nausea, photophobia, phonophobia and functional disabilities. A migraine treatment involving the use of a nonprescription combination of APAP/ASA/CAF in accordance with the present invention promises to have important cost and safety advantages over currently used prescription agents.

SUMMARY OF THE INVENTION

It is an object of the present invention to provide nonprescription compositions and methods to treat a migraine attack and the cluster of symptoms which are characteristic of migraine, including pain, nausea, photophobia, phonophobia and functional disability. In accordance with the present invention, migraine pain, and one or more of the symptoms of nausea, photophobia, phonophobia and functional disability associated with migraine attack, are alleviated and/or eliminated by treating a subject with a nonprescription composition comprising a combination of acetaminophen, aspirin and caffeine (APAP/ASA/CAF).

It is another object of the present invention to treat and alleviate migraine pain and one or more of the symptoms of migraine as mentioned above by providing a composition comprising the APAP/ASP/CAF combination in an amount effective to mitigate, alleviate or eliminate migraine pain and one or more of the symptoms of migraine.

It is yet another object of the present invention to use the above-described nonprescription analgesic comprising a combination of acetaminophen, aspirin and caffeine in amounts effective to provide abortive relief of migraine in the prodrome or aura phases which precede the onset of migraine-associated symptoms and the progression to an acute migraine. In accordance with this aspect of the invention, the analgesic combination is also used to provide symptomatic relief by aborting the development of full-blown migraine.

It is yet another object of the present invention to use the above-mentioned nonprescription analgesic to abort a migraine attack after migraine pain has developed. In accordance with this aspect of the invention, the analgesic combination is used not only to abort the pain stemming from a migraine attack, but also to abort at least one, preferably two or more, of the cluster of symptoms of nausea, photophobia, phonophobia and basic functional disabilities that are further associated with migraine attack.

It is a further object of the present invention to provide the nonprescription analgesic composition comprising acetaminophen, aspirin and caffeine in accordance with the foregoing, wherein the efficacy of the composition in effecting the reduction or elimination of migraine pain and/or its associated cluster of symptoms is similar to or at a parity with the efficacy of a similar dosing regimen of sumatriptan, i.e., sumatriptan succinate (Imitrex®, sold by Glaxo Wellcome), to reduce or eliminate migraine pain and/or its symptoms.

It is yet a further object of the present invention to provide the nonprescription analgesic as described above for effective use either prophylactically or therapeutically to prevent or treat, respectively, migraine pain and the cluster symptoms associated with migraine.

Yet another object of the present invention is eliminate the need for individuals suffering from migraine to re-dose or re-medicate after an effective dose of the aforementioned nonprescription analgesic composition comprising acetaminophen, aspirin and caffeine has been administered. Thus, in accordance with the present invention, a subject's need for rescue medication is obviated.

Further objects and advantages afforded by the present invention will be apparent from the detailed description hereinbelow.

DESCRIPTION OF THE DRAWINGS

The appended drawings of the figures are presented to further describe the present invention and to assist in its understanding through clarification of its various aspects.

FIG. 1A shows the percentage of tested individuals (i.e., pooled, efficacy-evaluable subjects) in which pain intensity was reduced to mild or none up to about six hours after the administration of a unit dose of the nonprescription analgesic combination containing acetaminophen, aspirin and caffeine, i.e., APAP/ASA/CAF, (closed circles) versus placebo (open circles).

FIG. 3A shows the percentage of tested individuals (i.e., pooled, efficacy-evaluable subjects) having the nausea symptom of migraine up to about six hours after treatment with a unit dose of the nonprescription analgesic combination containing acetaminophen, aspirin and caffeine, i.e., APAP/ASA/CAF, (closed circles) versus placebo (open circles).

FIG. 3B shows the percentage of tested individuals (i.e., pooled, efficacy-evaluable subjects) having the photophobia symptom of migraine up to about six hours after treatment with a unit dose of the nonprescription analgesic combination containing acetaminophen, aspirin and caffeine, i.e., APAP/ASA/CAF, (closed circles) versus placebo (open circles).

FIG. 3C shows the percentage of tested individuals (i.e., pooled, efficacy-evaluable subjects) having the phonophobia symptom of migraine up to about six hours after treatment with a unit dose of the nonprescription analgesic combination containing acetaminophen, aspirin and caffeine, i.e., APAP/ASA/CAF, (closed circles) versus placebo (open circles).

DETAILED DESCRIPTION OF THE INVENTION

Figure 1B:
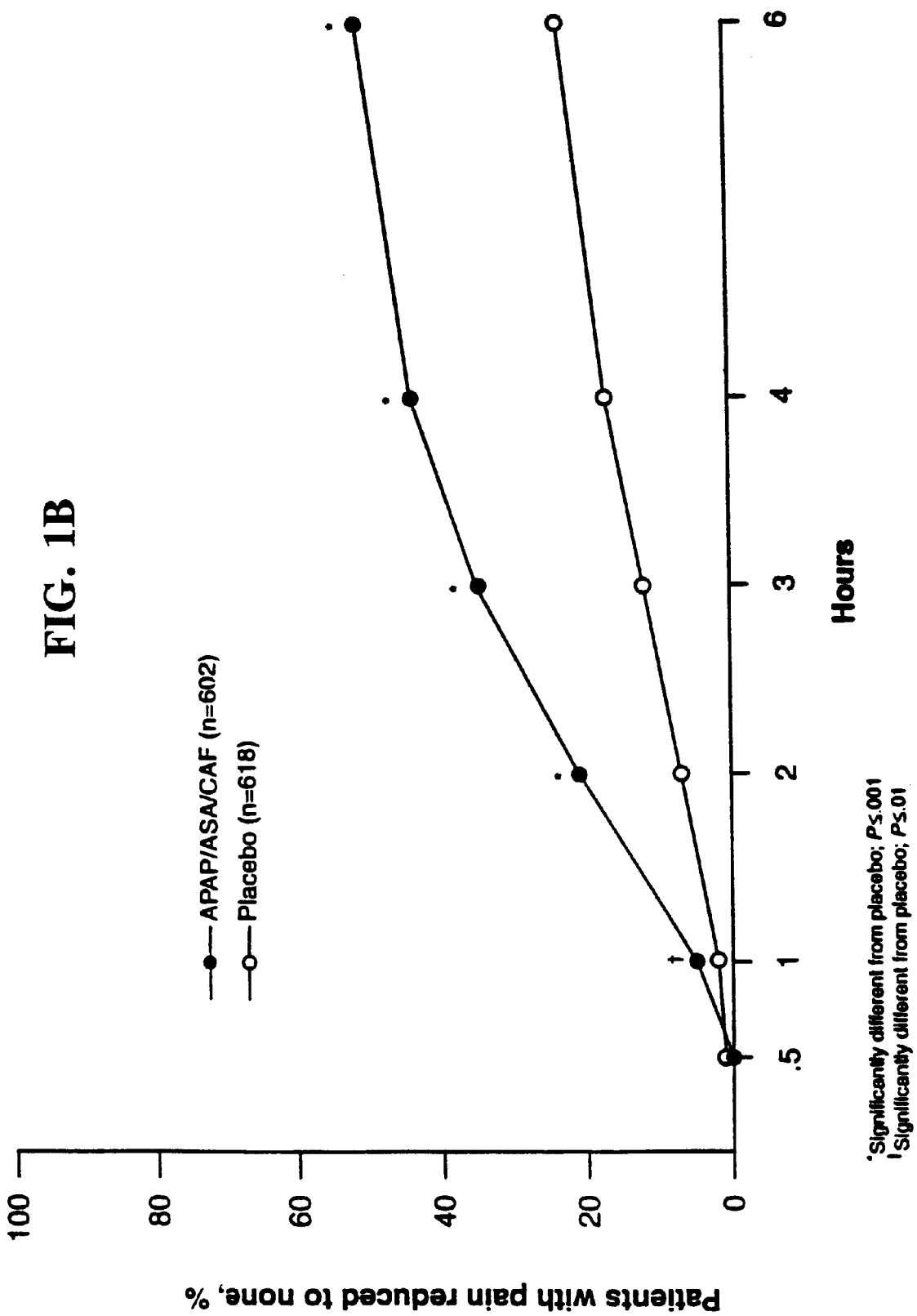
FIG. 1B shows the percentage of tested individuals (i.e., pooled, efficacy-evaluable subjects) in which pain intensity was reduced to none, up to about six hours after treatment with a unit dose of the nonprescription analgesic combination containing acetaminophen, aspirin and caffeine, i.e., APAP/ASA/CAF, (closed circles) versus placebo (open circles).

The present invention provides a composition and method for use in relieving the pain and symptoms characteristic of migraine attack. The composition is a nonprescription analgesic comprising a combination of acetaminophen, aspirin and caffeine (also termed herein APAP/ASA/CAF), the use of which has been shown by the present inventors to be clinically safe and efficacious in alleviating migraine pain and one or more of the cluster of symptoms that are characteristic of migraine attack.

The present invention provides the combination of acetaminophen, aspirin and caffeine (APAP/ASA/CAF) as a beneficial and advantageous nonprescription treatment for migraine. The nonprescription APAP/ASA/CAF analgesic combination reduces and relieves migraine pain in migraine sufferers. A particular but nonlimiting example of an APAP/ASA/CAF combination composition for use in accordance with the present invention is commercially-available, nonprescription Excedrin® Extra-Strength.

In general, the migraine condition, with or without aura, has a variety of characteristic features. Migraine attacks are episodic and self-limited. The duration of untreated or unsuccessfully-treated migraine attacks can be from several hours to several days (e.g., about four hours to about three days). Migraine attacks are relatively infrequent, with about seventy-five percent of migraine sufferers experiencing less than or equal to three attacks per month[1,3,4]. Common pain characteristics of migraines include pain in a unilateral location, with a pulsating quality. Pain is usually of moderate to severe intensity and is aggravated by routine physical activity. One or more of a cluster of symptoms is recognized to frequently accompany migraines, namely, nausea and/or vomiting, photophobia, phonophobia, and functional disability, i.e., difficulty in performing routine work-related and non-work-related tasks.

In one embodiment of the present invention, the APAP/ASA/CAF combination composition provides abortive relief of the symptoms of migraine, in the prodrome phase, or in the aura phase (when it occurs), which are known to precede an acute migraine attack and severe migraine pain. In accordance with this aspect of the invention, the analgesic combination is used in accordance with the invention to provide symptomatic relief by aborting the development of full-blown migraine attack.

It will be appreciated by the routine practitioner that the prodrome phase of a condition of migraine occurs before aura and before severe or throbbing migraine pain. Frequently during prodrome, the migraine sufferer experiences mood changes, lethargy and tiredness. It will also be appreciated that migrainous aura, which is experienced by about 20% of migraine sufferers, precedes severe migraine pain and throbbing. Aura involves distinctive auditory and visual distortions, which may involve visual scotomas or even hemianopia and speech abnormalities, that develop prior to severe migraine pain and throbbing. Without wishing to be bound by theory, migrainous aura is likely to be associated with a release of serotonin from platelets. An advantageous aspect of the use of the APAP/ASA/CAF combination in accordance with the present invention is its ability to abort a migraine attack before the migraine sufferer experiences intense, severe migraine pain and related discomforts.

In another embodiment of the present invention, the nonprescription APAP/ASA/CAF composition provides abortive relief of a migraine attack after the prodrome and/or aura phases and once migraine pain has developed. In accordance with this aspect of the invention, the analgesic combination is used not only to abort migraine pain that has developed, but also to abort one or more, and especially two or more, of the characteristic cluster of symptoms, namely, nausea, photophobia, phonophobia and basic functional disabilities, that are further associated with migraine and migraine pain that occur after the prodrome phase.

In accordance with the present invention, the effectiveness of the nonprescription APAP/ASA/CAF combination treatment of the present invention to alleviate and/or eliminate migraine pain and one or more of its cluster of associated symptoms is similar to or at a parity with a similar dosing schedule of sumatriptan, i.e., sumatriptan succinate (e.g., Imitrex®, Glaxo-Wellcome), (see Example 9). Both sumatriptan and the APAP/ASA/CAF combination treatment of the present invention are capable of prodromally aborting migraine. The similarities in the effectiveness of sumatriptan and the APAP/ASA/CAF combination analgesic used according to the present invention in providing migraine relief is unexpected, given that these active compounds have different mechanisms of action. For example, while sumatriptan inhibits serotonin receptor activity, the APAP/ASA/CAF combination is not known to work in a similar manner.

An additional advantage of the use of the combination of APAP/ASA/CAF to treat migraine pain and its symptoms in accordance with the present invention is that after taking an effective unit dose, a migraine sufferer is less likely to require rescue medication or redosing at the end of the dosing schedule, e.g., about 4 to 6 hours, due to the effectiveness of the treatment of the present invention in alleviating migraine pain and/or its associated symptoms (Examples 4 and 5).

For oral administration, a unit dose of the APAP/ASA/CAF combination composition according to the present invention is hereinafter defined as a pharmaceutically effective, migraine-treating amount of the APAP/ASA/CAF active components comprising from about 300 mg to about 600 mg, preferably about 400 mg to about 550 mg, and more preferably, about 500 mg of acetaminophen; about 300 mg to about 600 mg, preferably about 400 mg to about 550 mg, and more preferably, about 500 mg of aspirin; and about 100 to about 250, preferably about 125 to about 200, and more preferably about 130 mg of caffeine. For convenience, a unit dose is provided as two tablets, or the equivalent thereof, with each tablet, or the equivalent thereof, comprising one-half of the unit dose.

Pharmaceutical preparations containing the combination of APAP/ASA/CAF and conventional pharmaceutical carriers may be employed in suitable unit dosage forms, such as solids or liquids. Solid form preparations include, for example, tablets, pills, caplets, capsules, powders, dispersible granules, cachets, and suppositories. Preferred are tablets, pills, or capsules. Liquid form preparations include, for example, isotonic solutions, suspensions, or elixirs for oral administration or liquid solutions, suspensions, and emulsions for parenteral use. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

Tablets may contain the active ingredient in admixture with non-toxic, pharmaceutically-acceptable excipients which are suitable for the manufacture of tablets. These excipients may be, for example, inert diluents, for example, calcium carbonate, sodium carbonate, lactose, calcium phosphate or sodium phosphate; granulating or disintegrating agents, for example, maize starch or alginic acid; binding agents, for example, starch, gelatin, or acacia; and lubricating agents, for example, magnesium stearate or stearic acid. The tablets may be uncoated or they may be coated by known techniques to delay disintegration and absorption in the gastrointestinal tract, and thereby provide a sustained action for a longer period of time.

In addition, tablets may contain the active preparation as a powder or granules, for example, a lyophilized powder or granules optionally mixed with binders, lubricants, inert diluents, or surface-active or dispersing agents, and may be formed by compression or by mouling in inert liquid diluent. Such tablets may be optionally scored and/or coated. Capsules and cachets may contain the active compounds alone or in admixture with one or more accessory ingredients. Capsules may also contain the active ingredients in aqueous or oleaginous solution, suspension, or emulsion, optionally in association with accessory ingredients.

Formulations for oral use may also be presented as hard gelatin capsules wherein the APAP/ASA/CAF active ingredients are mixed with an inert solid diluent, for example, calcium carbonate, calcium phosphate, or kaolin, or as soft gelatin capsules, wherein the active ingredients are mixed with an oil medium, for example, arachis oil, liquid paraffin, or olive oil.

Additional formulations suitable for other modes of administration, such as suppositories, may include binders and carriers, for example, polyalkylene glycols or triglycerides.

Aqueous suspensions contain the active ingredients in admixture with excipients suitable for the manufacture of aqueous suspensions. Nonlimiting examples of such excipients include suspending agents, for example, sodium carboxymethyl cellulose, methylcellulose, hydroxypropylmethylcellulose, sodium alginate, polyvinylpyrrolidone, gum tragacanth, and gum acacia. Dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan monooleate. The aqueous suspensions may also contain one or more preservatives, for example, ethyl or n-propyl p-hydroxy benzoate, one or more coloring agents, one or more flavoring agents, and one or more sweetening agents, such as sucrose, saccharin, or sodium or calcium cyclamate.

Several modes and routes of administration may be used to administer the APAP/ASA/CAF composition in accordance with the present invention. For example, the composition in appropriate dosage form may be made available for oral, sublingual, rectal, intravenous, intramuscular, parenteral, rectal suppository or inhaler use. Preferred is oral administration.

The dosing interval for the unit dose is preferably daily, about every four to six hours, preferably every six hours, with a maximum daily dose of eight tablets and a maximum duration of use of about ten days or less.

In accordance with the present invention and as described in the examples hereinbelow, in each of three specifically designed and controlled clinical studies carried out to evaluate the efficacy of the use of the APAP/ASA/CAF combination to treat migraine attack, significantly greater reductions in migraine pain intensity from about one to six hours postdose were observed in migraine sufferers to whom the APAP/ASA/CAF combination had been administered compared with migraine sufferers to whom a placebo had been administered. Specifically, at two hours postdose, pain intensity was reduced to mild or none in 59% (i.e., 357/602) of APAP/ASA/CAF-treated migraine sufferers compared with 33% (i.e., 203/618) of placebo-treated migraine sufferers (P<0.001; 95% confidence interval [CI]; APAP/ASA/CAF 55%–63%, placebo 29%–37%). At six hours postdose, 79% versus 52%, respectively, had pain reduced to mild or none (P<0.001, CI 75%–82% versus 48%–56%). In addition, by six hours postdose, 51% (i.e., 306/602) of APAP/ASA/CAF-treated migraine sufferers were pain-free compared with 23% (i.e., 145/618) of placebo-treated migraine sufferers (P<0.001; 95% CI, APAP/ASA/CAF 47%–55%, placebo 20%–27%). Other migraine-related characteristics, such as nausea, photophobia, phonophobia and functional disability were significantly improved at two to six hours after treatment of migraine sufferers with the APAP/ASA/CAF combination compared with placebo (P≦0.01). Thus, the nonprescription combination of acetaminophen, aspirin, and caffeine was highly effective for the treatment of migraine pain, as well as for alleviating the symptoms of nausea, photophobia; phonophobia, and functional disability associated with migraine attacks. APAP/ASA/CAF also has an excellent safety profile and is well tolerated.

Treatment differences for the prospectively-defined outcomes measured in these studies were highly significant in favor of the APAP/ASA/CAF combination analgesic in both the population-based study (Study 1) and in the studies which used primarily conventional recruiting methods (Study 2 and Study 3), as described in the examples herein. Significant differences favoring APAP/ASA/CAF were found in each of the three studies from about one to six hours postdose. Significant differences between APAP/ASA/CAF combination treatment versus placebo were observed as early as 0.5 hours postdose for pain intensity difference from baseline and for pain reduced to mild or none in two studies, as well as in the pooled analysis. Subjects in the APAP/ASA/CAF-treatment groups also experienced significant improvements in ability to perform usual activities at 1 hour postdose and at all timepoints thereafter.

Although migraine-specific prescription agents are known to provide relief for the migraine symptom complex including nausea, photophobia and phonophobia, the present invention provides a safe, economical and efficacious nonprescription alternative to prescription medications. The combination of APAP/ASA/CAF used according to the present invention produced statistically significant improvement in nausea, photophobia, and phonophobia. Improvement in these associated symptoms in the pooled analysis became statistically significant at 30 minutes after dosing. Further, the benefits of the APAP/ASA/CAF combination in treating migraines were demonstrated in subjects with moderate to severe pain and significant impairment of function.

The present invention has important advantages and implications for clinical practice and for migraine and headache health-care policy. Most approved prescription drugs for migraine are expensive and many have therapy-limiting side effects and contraindications. In accordance with the present invention, APAP/ASA/CAF, a nonprescription combination analgesic with a favorable safety profile, effectively treats the pain, disability, and associated symptoms of migraine. The use of this combination provides a safe and cost-effective treatment alternative for patients with migraine.

EXAMPLES

The examples as set forth herein are meant to exemplify the various aspects of carrying out the present invention and are not intended to limit the invention in any way.

Three independent, double-blind, randomized, parallel group, placebo-controlled studies were designed and carried out to assess the effectiveness of the nonprescription combination of APAP/ASA/CAF for alleviating acute migraine pain and its associated symptoms. The protocols and results are set forth in the Examples presented hereinbelow.

Example 1

Methods

Subjects

Three studies, conducted between August 1995 and June 1996, utilized a uniform double-blind, randomized, parallel-group, placebo-controlled design, and differed only in the methods of subject recruitment. Study 1, a single-center trial, used random-digit dialing exclusively to identify potentially eligible subjects[19]. Study 2 and Study 3 were multicenter trials which relied on both conventional (77%) (e.g., private practice patients, referrals, local advertising) and random-digit (23%) methods for recruiting.

Inclusion and exclusion criteria for the three studies were identical. Patients met International Headache Society (IHS) diagnostic criteria for migraine without aura or migraine with aura[20], were at least 18 years old, were in good general health, and had experienced migraine attacks at least once every two months but no more than six times monthly. Migraine pain was of at least moderate intensity when left untreated. Subjects who were usually incapacitated (i.e., required bedrest for their attacks) were excluded. Subjects who experienced vomiting ≧20% of the time were also excluded because of the probability that they might vomit and not absorb the study medication. Nausea was not an exclusion. Written, informed consent was obtained from all subjects. The protocol and consent forms were approved by an Institutional Review Board for each clinic.

To ensure that all subjects actually suffered from migraine, each provided a complete medical history, including a semistructured diagnostic headache interview, and underwent a physical examination and neurological evaluation by a study clinician. Subjects were trained to complete the study diary.

Example 2

Study Design

Protocol

At Visit 1, qualified subjects were randomly assigned (1:1 ratio) according to a computer-generated randomization schedule to receive a bottle of double-blinded study medication containing either 2 tablets of an unbranded composition comprising a combination of acetaminophen 250 mg per tablet, aspirin 250 mg per tablet and caffeine 65 mg per tablet, or two identical-appearing placebo tablets, to treat the pain of one acute self-recognized migraine attack. If the pain and symptom profile met the definition of migraine, if the migraine pain was of at least moderate intensity, and if the attack was otherwise eligible, the subject was instructed to take the study medication. Subjects were asked not to take rescue medication for 2 hours, if possible. All treatment information was maintained in a blinded form until after the database was locked and all queries were resolved.

Efficacy Measurements

The primary efficacy measurements were pain intensity difference (PID) from baseline and the percentage of subjects with pain reduced to mild or none at 2 hours postdose. At baseline, subjects rated their pain intensity, functional disability, nausea, vomiting, photophobia and phonophobia. They also rated these symptoms, together with pain relief, at 0.5, 1, 2, 3, 4, and 6 hours postdose. Subjects rated pain intensity using a four-point scale (0=no pain; 1=mild pain; 2=moderate pain; and 3=severe pain). They rated pain relief from 0 to 4 (0=no relief; 1=a little relief; 2=some relief; 3=a lot of relief; and 4=complete relief). They rated functional disability from 0 to 4 (0=none; 1=usual activities require a little additional effort; 2=usual activities require some additional effort; 3=usual activities require a great deal of additional effort; and 4=inability to perform usual activities). Nausea, photophobia and phonophobia were rated separately using a 0 to 3 scale (0=none; 1=mild; 2=moderate; and 3=severe intensity) for each symptom.

Migraine sufferers provided a global evaluation of analgesic efficacy at the end of the 6-hour treatment period, or when they took rescue medication. The investigators provided similar evaluations. Global evaluations were rated from 1 to 5 (1=poor; 2=fair; 3=good; 4=very good; and 5=excellent).

Other efficacy variables were derived from the scores recorded by subjects. Such efficacy variables included Pain Intensity Difference (PID); percentage of subjects with pain intensity reduced to mild or none; percentage of subjects considered to be pain-free; and percentage of subjects who required medication during the 6-hour evaluation period.

Safety Assessments

Adverse experiences were recorded in the diary by the subjects and elicited at Visit 2 by the investigators. The intensity, duration and relation to the study drug were recorded. Clinical laboratory data were not systematically collected.

Statistical Analysis

For each study, a sample size of 200 subjects per arm provided at least 85% power to detect a clinically meaningful difference of at least 15% in the proportion of subjects with pain reduced to mild or none (two-sided, alpha=0.05).

Treatment group comparability was assessed using analysis of variance (ANOVA) for quantitative variables (e.g., age) and chi-square tests for categorical variables (e.g., gender). The two treatment groups were compared in each study with respect to demographics and baseline characteristics.

Data missing for any scheduled evaluation period in otherwise evaluable subjects (e.g., subject fell asleep) were interpolated. For example, if the 0.5 hour observation was missing, it was replaced by the average of the baseline and the 1-hour observation value. For subjects requiring rescue medication, post-rescue medication severity scores for pain intensity, functional ability, and nausea were assigned either the baseline or the last recorded value, whichever was the most severe. Post-rescue medication pain relief scores were assigned "No Relief."

The primary efficacy analysis was based on the efficacy-evaluable subject population. The data were also analyzed on an Intent-to-Treat (ITT) basis. Each study was analyzed separately. The results of the independent studies were tested for poolability.

Comparisons between the two treatment groups were made at each timepoint using an analysis of covariance (ANCOVA) model for changes from baseline severity in pain intensity, functional ability, and severity of nausea, photophobia, and phonophobia. An ANOVA model was used to compare the treatments with respect to pain relief and the subject's global evaluation at 6 hours postdose and the investigator's global evaluation at Visit 2. The Cochran-Mantel-Haenszel test, stratified by baseline pain intensity, was used to analyze the percentage of subjects with pain intensity reduced to mild or none, percentage of subjects with pain intensity reduced to none, and percentage of subjects who remedicated. Statistical significance was declared if the P value was ≦0.05.

Example 3

Subject Population

Of the 1357 subjects randomized in the three studies, 1250 (92%) took the study medication of a combination composition of APAP/ASA/CAF. Baseline or postdose evaluations were missing for two APAP/ASA/CAF-treated subjects and one placebo-treated subject; consequently, these subjects were excluded from all efficacy evaluations, leaving a total of 1247 subjects in the Intent-to-Treat (ITT) group. The ITT group and efficacy-evaluable data sets differed by only 27 subjects (1247 ITT, 1220 efficacy-evaluable). The 27 subjects not included in the efficacy evaluable analysis were comprised of 14 individuals who treated a headache/head pain which did not meet protocol criteria for migraine, 9 who did not complete their evaluations at 2 hours postdose, and 4 who did not take the entire dose of study medication.

The two treatment groups had similar demographic profiles and past migraine histories (Table 1) in each of the studies. Table 1 shows that the subjects studied were truly migraineurs. Without treatment, usual migraine pain was moderate in 28%, severe in 70%, and incapacitating in <1%; 39% had reported moderate and 49% severe migraine-related disability. In 63%, migraine attack or headaches were frequently or always accompanied by nausea. Migraine was treated with nonprescription medications by 65% of subjects, with prescription medications by 12.5%, with both nonprescription and prescription medications by 21%, and with no medication at all by 1.5%. Symptom profiles for the treated migraine pain in the APAP/ASA/CAF active and placebo groups for all 3 individual studies and the pooled analysis were comparable at baseline (Table 2).

TABLE 1

Demographics and Past Migraine History of Efficacy-Evaluable Subjects

| | Study 1 | | Study 2 | | Study 3 | | Pooled | |
|---|---|---|---|---|---|---|---|---|
| | APAP/ASA/CAF (n = 187) | Placebo (n = 191) | APAP/ASA/CAF (n = 206) | Placebo (n = 221) | APAP/ASA/CAF (n = 209) | Placebo (n = 206) | APAP/ASA/CAF (n = 602) | Placebo (n = 618) |
| Mean age (yrs) | 35.3 | 35.8 | 37.8 | 35.9 | 37.8 | 37.6 | 37.0 | 36.4 |
| Gender (%) | | | | | | | | |
| Male | 25 | 23 | 24 | 19 | 17 | 17 | 22 | 20 |
| Female | 75 | 77 | 76 | 81 | 83 | 83 | 78 | 80 |
| Race (%)* | | | | | | | | |
| White | 78 | 85 | 84 | 88 | 90 | 89 | 84 | 88 |
| Black | 21 | 15 | 11 | 5 | 4 | 7 | 11 | 9 |
| Other | 1 | 0 | 5 | 6 | 6 | 4 | 4 | 4 |
| Migraine type (%) | | | | | | | | |
| Without aura | 86 | 85 | 77 | 75 | 82 | 82 | 81 | 80 |
| With aura | 14 | 15 | 23 | 25 | 18 | 18 | 19 | 20 |
| Usual pain without treatment (%)* | | | | | | | | |
| None/Mild | 0 | 0 | 0 | 0 | 0 | 0 | 0 | 0 |
| Moderate | 29 | 29 | 21 | 25 | 34 | 28 | 28 | 27 |
| Incapacitating | 0 | 1 | 0 | <1 | <1 | <1 | <1 | — |
| Severe | 71 | 71 | 76 | 71 | 62 | 68 | 70 | 70 |
| Unknown+ | 0 | 0 | 2 | 4 | 3 | 4 | 2 | 3 |
| Usual disability without treatment (%)* | | | | | | | | |
| None | 3 | 1 | 1 | 3 | 0 | 0 | 1 | 1 |
| Mild | 13 | 9 | 7 | 11 | 5 | 4 | 8 | 8 |
| Moderate | 47 | 47 | 35 | 30 | 41 | 36 | 41 | 37 |
| Severe | 37 | 41 | 54 | 51 | 51 | 55 | 48 | 49 |
| Incapacitating | 0 | 1 | <1 | 1 | 0 | 0 | <1 | 1 |
| Unknown+ | 0 | 1 | 2 | 4 | 3 | 4 | 2 | 3 |
| Nausea with attacks (%)* | | | | | | | | |
| Always | 9 | 9 | 15 | 15 | 32 | 29 | 19 | 18 |
| Frequently | 42 | 46 | 51 | 47 | 39 | 42 | 44 | 45 |
| Rarely | 27 | 25 | 20 | 23 | 21 | 18 | 22 | 22 |
| Never | 22 | 21 | 14 | 15 | 9 | 11 | 15 | 16 |
| Usual pharmacologic treatment (%)* | | | | | | | | |
| None | 1 | 2 | 1 | 1 | 1 | 2 | 1 | 2 |
| Nonprescription only | 84 | 82 | 59 | 57 | 59 | 52 | 67 | 63 |
| Prescription only | 5 | 4 | 12 | 16 | 19 | 18 | 12 | 13 |
| Both | 10 | 12 | 28 | 26 | 22 | 28 | 20 | 22 |

*Percentages may not add to 100 due to rounding.
+Statistical analysis did not include subjects with missing data.

TABLE 2

Characteristics of Treated Migraines, Pooled Data

|  | APAP/ASA/CAF n = 602 (%) | Placebo n = 618 (%) |
|---|---|---|
| Migraine without aura | 499 (83) | 515 (83) |
| Pain on one side of the head | 366 (61) | 353 (57) |
| Head pain pulsating | 424 (70) | 456 (74) |
| Pain aggravated by activity | 421 (70) | 445 (72) |
| Migraine with aura | 103 (17) | 103 (17) |
| Pain on one side of head | 71 (17) | 76 (12) |
| Head pain pulsating | 93 (15) | 88 (14) |
| Pain aggravated by activity | 86 (14) | 88 (14) |
| Baseline pain |  |  |
| Moderate | 400 (66) | 413 (67) |
| Severe | 202 (34) | 205 (33) |
| Functional ability |  |  |
| Ability to perform all activities as usual | 21 (3) | 12 (2) |
| A little additional effort required | 83 (14) | 91 (15) |
| Some additional effort required | 285 (47) | 292 (47) |
| Great deal of additional effort | 184 (31) | 185 (30) |
| Unable to perform usual activities | 28 (5) | 37 (6) |
| Unknown | 1 (<1) | 1 (<1) |
| Nausea |  |  |
| None | 241 (40) | 250 (40) |
| Mild | 253 (42) | 259 (42) |
| Moderate | 95 (16) | 103 (17) |
| Severe | 13 (2) | 6 (1) |
| Vomiting |  |  |
| No | 589 (98) | 613 (99) |
| Yes | 13 (2) | 5 (1) |
| Number of subjects with: |  |  |
| Both photophobia and phonophobia | 522 (87) | 558 (90) |
| Photophobia only | 51 (8) | 25 (4) |
| Phonophobia only | 15 (2) | 19 (3) |
| Neither | 13 (2) | 15 (2) |
| Unknown | 1 (<1) | 1 (<1) |

No statistically significant treatment-by-study interactions were detected for any of the primary efficacy variables at any time point. Isolated significant interactions were detected for functional ability (hour 2) and photophobia (hours 0.5, 1); however, the interactions were quantitative in nature rather than qualitative, and therefore do not alter the results. Accordingly, data were pooled to optimally summarize study results. Efficacy and safety results are presented for the three studies separately and for the pooled analysis.

Example 4

Pain Intensity and Pain Relief

In each of the three studies, subjects treated with the composition comprising a combination of APAP/ASA/CAF had significantly higher mean PID scores than did subjects taking placebo at all timepoints from 1 hour to 6 hours postdose (P<0.001). In the pooled analysis and in Study 1 and Study 3, subjects who received active treatment also had significantly higher mean PID scores than did placebo subjects beginning at the 0.5 hour timepoint (P≦0.017).

A larger proportion of APAP/ASA/CAF-treated subjects experienced a reduction in migraine pain intensity to mild or none, starting 1 hour postdose and continuing to the 6-hour timepoint in all three studies (P≦0.002). In the pooled analysis, differences were statistically significant at 0.5 hours postdose (P=0.014) and at all subsequent timepoints (P<0.001) (FIG. 1A). Pooled data showed that at 2 hours postdose, 59% (i.e., 357/602) of all APAP/ASA/CAF-treated subjects had mild or no migraine pain compared with 33% (i.e., 203/618) of all placebo-treated subjects (P<0.001; 95% CI, APAP/ASA/CAF 55%–63%, placebo 29%–37%). Corresponding percentages at least 6 hours postdose were 79% (i.e., 473/602) and 52% (i.e., 319/618), respectively, (P<0.001 CI, 75%–82% versus 48%–56%) (Table 3).

A significantly larger proportion of the APAP/ASA/CAF-treated subjects were pain free compared with placebo, starting at 2 hours postdose and continuing to the 6-hour timepoint (P≦0.008). Significance was also detected by 1 hour postdose in the pooled analysis (P=0.002), (FIG. 1B), and in Study 3 (P=0.004). At two hours postdose, 21% (i.e., 125/602) of all APAP/ASA/CAF-treated subjects had no migraine head pain compared with 7% (i.e., 44/618) of all placebo-treated subjects (P<0.001; 95% CI; APAP/ASA/CAF 18%–24%, placebo 5%–9%) (Table 3).

TABLE 3

Summary of Results for Efficacy-Evaluable Subjects Taking APAP/ASA/CAF Combination at 2 Hours and 6 Hours Postdose

|  | Study 1 | | Study 2 | | Study 3 | | Pooled | |
|---|---|---|---|---|---|---|---|---|
|  | APAP/ASA/CAF (n = 187) | Placebo (n = 191) | APAP/ASA/CAF (n = 206) | Placebo (n = 221) | APAP/ASA/CAF (n = 209) | Placebo (n = 206) | APAP/ASA/CAF (n = 602) | Placebo (n = 618) |
| Results at 2 hours |  |  |  |  |  |  |  |  |
| Mean PID (S.D.) | 1.2* (0.95) | 0.5 (0.96) | 0.9* (0.85) | 0.4 (0.89) | 0.9* (0.93) | 0.4 (0.83) | 1.0* (0.91) | 0.4 (0.89) |
| % Subjects with pain reduced to mild or none | 64* | 37 | 59* | 31 | 56* | 31 | 59* | 33 |
| Mean PAR (S.D.) | 2.0* (1.40) | 1.0 (1.16) | 1.6* (1.34) | 0.9 (1.20) | 1.7* (1.45) | 0.8 (1.10) | 1.8* (1.41) | 0.9 (1.16) |
| % Subjects with no pain | 26* | 7 | 17† | 9 | 21* | 5 | 21* | 7 |
| % Subjects without nausea | 73 | 66 | 57 | 57 | 59† | 46 | 63† | 56 |
| % Subjects without photophobia | 40* | 14 | 29† | 19 | 35* | 17 | 35* | 17 |
| % Subjects without phonophobia | 42* | 17 | 32† | 20 | 36* | 20 | 37* | 19 |
| % Subjects with little or no functional disability | 66* | 34 | 59† | 35 | 53† | 33 | 59* | 34 |

TABLE 3-continued

Summary of Results for Efficacy-Evaluable Subjects Taking APAP/ASA/CAF Combination at 2 Hours and 6 Hours Postdose

|  | Study 1 | | Study 2 | | Study 3 | | Pooled | |
| --- | --- | --- | --- | --- | --- | --- | --- | --- |
|  | APAP/ASA/CAF (n = 187) | Placebo (n = 191) | APAP/ASA/CAF (n = 206) | Placebo (n = 221) | APAP/ASA/CAF (n = 209) | Placebo (n = 206) | APAP/ASA/CAF (n = 602) | Placebo (n = 618) |
| Results at 6 hours | | | | | | | | |
| Mean PID (S.D.) | 1.6* | 0.8 | 1.3* | 0.6 | 1.2* | 0.6 | 1.4* | 0.6 |
|  | (1.07) | (1.25) | (1.09) | (1.10) | (1.14) | (1.17) | (1.11) | (1.17) |
| % Subjects with pain reduced to mild or none | 82* | 55 | 78* | 48 | 76* | 53 | 79* | 52 |
| Means PAR (S.D.) | 2.7* | 1.4 | 2.2* | 1.2 | 2.2* | 1.3 | 2.4* | 1.3 |
|  | (1.64) | (1.69) | (1.67) | (1.57) | (1.70) | (1.59) | (1.69) | (1.62) |
| % Subjects with no pain | 61* | 28 | 47* | 21 | 45* | 21 | 51* | 23 |
| % Subjects without nausea | 80† | 68 | 72† | 57 | 72* | 56 | 74* | 60 |
| % Subjects without photophobia | 66* | 35 | 58* | 27 | 52* | 33 | 58* | 31 |
| % Subjects without phonophobia | 66* | 35 | 57* | 31 | 54* | 34 | 59* | 33 |
| % Subjects with little or no functional disability | 75* | 45 | 69* | 39 | 63* | 38 | 69* | 41 |

*P ≦ .001;
†P = .01; (significantly different from placebo).
PID = pain intensity difference; PAR = pain relief By six hours after treatment with a unit dose of the APAP/ASA/CAF combination treatment versus placebo, 51% (i.e., 306/602) of subjects receiving active APAP/ASA/CAF treatment and 23% (i.e., 145/618) of subjects receiving placebo were free of pain (P<0.001; 95% CI; APAP/ASA/CAF 47%–55%, placebo 20%–27%) (Table 4).

Mean pain relief scores for APAP/ASA/CAF were significantly higher in the individual studies and in the pooled analysis at all timepoints from 0.5 hours to 6 hours postdose (P<0.001), except for Study 2 at 0.5 hours. Analysis of these primary efficacy measurements using the ITT population produced essentially identical results.

Example 5

Rescue Medication

In the pooled analysis, the proportion of subjects who required rescue medication was significantly greater in the placebo group than in the APAP/ASA/CAF-treated group, from 3 to 6 hours postdose (P<0.001). For example, by hour 6, only 12.5% (i.e., 75/602) of APAP/ASA/CAF-treated subjects needed to remedicate, compared with 27% (i.e., 168/618) of placebo treated subjects (P<0.001; 95% CI; APAP/ASA/CAF 10%–15%, placebo 24%–31%).

Example 6

Global Evaluations

Global evaluations of migraine pain relief by both subjects and investigators were significantly higher for the use of the APAP/ASA/CAF treatment in accordance with the present invention than for the use of placebo (P<0.001). Investigators' global evaluations were good to excellent in 51% of subjects in the APAP/ASA/CAF-treatment group, compared with 20% in the placebo group (P<0.001; 95% CI; 47% to 55% versus 17%–23%). Results were similar for subjects' global evaluations.

Example 7

Effects on Other Migraine Characteristics

Figure 2:
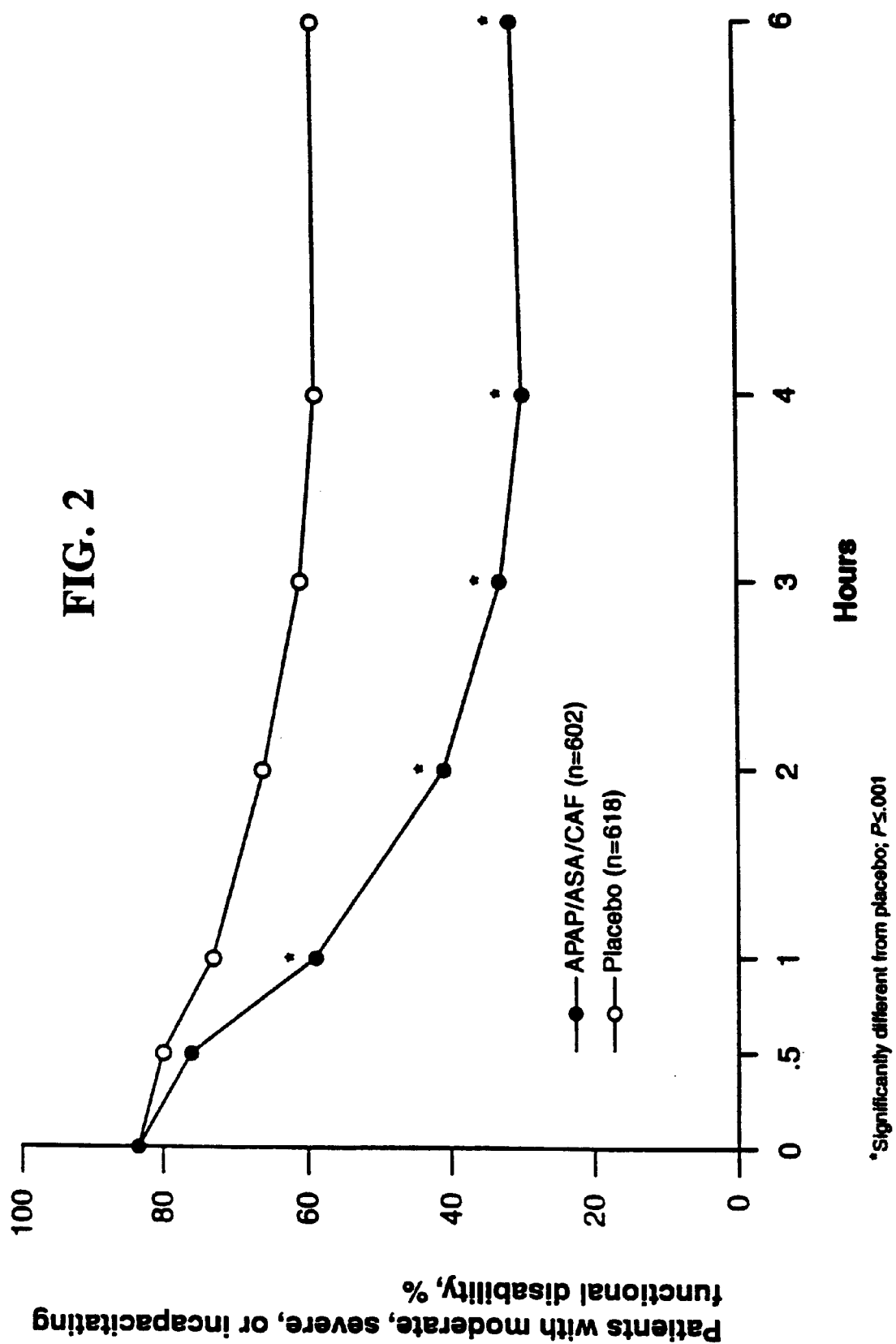
FIG. 2 shows the percentage of tested individuals (i.e., pooled, efficacy-evaluable subjects) in whom moderate, severe or incapacitating functional disabilities were apparent up to about six hours after the administration of a unit dose of the nonprescription analgesic combination containing acetaminophen, aspirin and caffeine, i.e., APAP/ASA/CAF, (closed circles) versus placebo (open circles). Moderate, severe or incapacitating functional disability relates to whether the test individuals required some or a great deal of additional effort to perform usual work-related or day-to-day activities, or if the individuals were unable to perform usual activities after treatment with the APAP/ASA/CAF combination versus a placebo control.

The percentage of subjects with restoration of function (able to perform activities with little or no additional effort) was significantly higher in the APAP/ASA/CAF-treated group than in the placebo-treated group in the pooled analysis (P<0.001), and in each study separately (P≦0.006) from 1 hour postdose to the 6-hour timepoint, and at 0.5 hours postdose in Study 1 (P=0.044) (FIG. 2).

TABLE 4

Cumulative Percentage of Efficacy-evaluable Subjects with Migraine Pain Reduced to Mild or None and Pain-Free After Treatment with Acetaminophen/Aspirin/Caffeine of the Present Invention versus Placebo

|  | Study 1 | | | Study 2 | | | Study 3 | | | Pooled | | |
| --- | --- | --- | --- | --- | --- | --- | --- | --- | --- | --- | --- | --- |
| Time (hrs) | APAP/ASA/CAF (n = 187) | Placebo (n = 191) | p value | APAP/ASA/CAF (n = 206) | Placebo (n = 221) | p value | APAP/ASA/CAF (n = 209) | Placebo (n = 206) | p value | APAP/ASA/CAF (n = 602) | Placebo (n = 618) | p value |
| Pain Reduced to Mild or None | | | | | | | | | | | | |
| 0.5 | 11 | 6 | .096 | 11 | 9 | .364 | 13 | 8 | .087 | 11 | 7 | .014 |
| 1 | 42 | 18 | <.001 | 33 | 20 | .002 | 38 | 17 | <.001 | 38 | 19 | <.001 |
| 2 | 64 | 37 | <.001 | 59 | 31 | <.001 | 56 | 31 | <.001 | 59 | 33 | <.001 |
| 3 | 75 | 46 | <.001 | 68 | 38 | <.001 | 67 | 40 | <.001 | 70 | 41 | <.001 |
| 4 | 80 | 51 | <.001 | 75 | 44 | <.001 | 73 | 49 | <.001 | 76 | 48 | <.001 |
| 6 | 82 | 55 | <.001 | 78 | 48 | <.001 | 76 | 53 | <.001 | 79 | 52 | <.001 |

TABLE 4-continued

Cumulative Percentage of Efficacy-evaluable Subjects with Migraine Pain Reduced to Mild or None and Pain-Free After Treatment with Acetaminophen/Aspirin/Caffeine of the Present Invention versus Placebo

| | Study 1 | | | Study 2 | | | Study 3 | | | Pooled | | |
|---|---|---|---|---|---|---|---|---|---|---|---|---|
| Time (hrs) | APAP/ ASA/CAF (n = 187) | Placebo (n = 191) | p value | APAP/ ASA/CAF (n = 206) | Placebo (n = 221) | p value | APAP/ ASA/CAF (n = 209) | Placebo (n = 206) | p value | APAP/ ASA/CAF (n = 602) | Placebo (n = 618) | p value |
| | | | | | | Pain Free | | | | | | |
| 0.5 | 1 | 1 | .979 | 0 | 2 | .052 | 9 | 0 | NA | <1 | 1 | .118 |
| 1 | 6 | 3 | .108 | 16 | 4 | .245 | 5 | 0 | .004 | 5 | 2 | .002 |
| 2 | 26 | 7 | <.001 | 17 | 9 | .008 | 21 | 5 | <.001 | 21 | 7 | <.001 |
| 3 | 43 | 15 | <.001 | 29 | 11 | <.001 | 33 | 9 | <.001 | 35 | 12 | <.001 |
| 4 | 54 | 22 | <.001 | 39 | 16 | <.001 | 39 | 15 | <.001 | 44 | 17 | <.001 |
| 6 | 61 | 28 | <.001 | 47 | 21 | <.001 | 45 | 21 | <.001 | 51 | 23 | <.001 |

Although subjects who vomited $\geq 20\%$ of the time were excluded from Studies 1–3, 60% had nausea at baseline. The percentage of subjects without nausea was significantly higher in the APAP/ASA/CAF-treatment group than in the placebo-treated group, from 1 to 6 hours postdose in Study 3 ($P \leq 0.047$); from 3 to 6 hours postdose in Study 1 ($P \leq 0.027$); and from 4 to 6 hours postdose in Study 2 ($P \leq 0.024$). In the pooled analysis, the proportion of subjects without nausea was significantly greater in the APAP/ASA/CAF-treatment group than in the placebo-treatment group, from 2 to 6 hours postdose ($P \leq 0.010$) (FIG. 3A).

The pooled analysis also showed that the percentage of subjects without photophobia or phonophobia was significantly larger in the APAP/ASA/CAF-treated group than in the placebo-treated group, from 1 hour postdose through the 6-hour timepoint ($P \geq 0.001$) (FIGS. 3B and 3C).

Example 8

Safety Results

No serious adverse experiences (AEs) were reported in any of the studies and the incidence of AEs considered to be severe was low (2%) and similar in the two treatment groups across the 3 studies (12/618 APAP/ASA/CAF-treated subjects; 11/632 placebo-treated subjects). One placebo-treated subject experienced vomiting and chills that resulted in discontinuation from Study 2. AEs with >1% incidence were few and expected. Those with a higher incidence than that seen in placebo subjects were nausea (4.9% versus 1.7%), nervousness (4.4% versus 0.8%), and dizziness (2.8% versus 1.1%). Interestingly, significantly more placebo-treated subjects experienced vomiting than those on active treatment: 1.6% (10/632) placebo-treated subjects versus 0.2% (1/618) APAP/ASA/CAF-treated subjects (P=0.001). No AEs different from those previously associated with single doses of aspirin, acetaminophen, or caffeine were seen in these studies.

Example 9

In this example, Table 5 presents a comparison of the pain relief or pain elimination afforded at 2 hours, 4 hours, or 6 hours postdose of sumatriptan (Imitrex®, 100 mg) and the APAP/ASA/CAF combination treatment in accordance with the present invention (unit dose, 2 tablets: 500 mg APAP; 500 mg ASA; 130 mg CAF). The results presented in Table 5 for the APAP/ASA/CAF combination treatment of the present invention are pooled values from studies 1, 2, and 3 as described hereinabove and as specifically shown in Table 3. The sumatriptan (Imitrex®) studies and data are reported and specifically described in the *Physician's Desk Reference,* (PDR), 51st Edition, Medical Consultant: R. Arky, MD, Medical Economics Company, Inc., Montvale, N.J., pp. 1099–1103 and Table 1, p. 1100, 1997. According to the PDR publication, the Imitrex® study design consisted of two controlled clinical studies (Study 1 and Study 2) to evaluate single doses of oral sumatriptan Imitrex®) in a total of 446 patients with migraine attacks who were experiencing moderate or severe pain and one or more symptoms of nausea, photophobia, or clinical disability (Ibid., Table 1).

TABLE 5

Dose Response Efficacy of Pain Relief from Sumatriptan (Imitrex ®) Tablet Versus APAP/ASA/CAF Combination Treatment of the Present Invention

| | Imitrex ® (Tablet) Study 1 | | Imitrex ® (Tablet) Study 2 | | APAP/ASA/CAF Combination of Present Invention | |
|---|---|---|---|---|---|---|
| | Placebo n = 65 | 100 mg n = 66 | Placebo n = 47 | 100 mg n = 46 | Placebo n = 618 | Unit Dose* n = 602 |
| Results at 2 hours | | | | | | |
| Patients with pain relief (grade 0/1) | 26% | 56% | 17% | 57% | 33% | 59% |
| Patients with no pain | 8% | 23% | 6% | 24% | 7% | 21% |
| Results at 4 hours | | | | | | |

TABLE 5-continued

Dose Response Efficacy of Pain Relief from Sumatriptan (Imitrex ®) Tablet
Versus APAP/ASA/CAF Combination Treatment of the Present Invention

|  | Imitrex ® (Tablet) Study 1 | | Imitrex ® (Tablet) Study 2 | | APAP/ASA/CAF Combination of Present Invention | |
|---|---|---|---|---|---|---|
|  | Placebo n = 65 | 100 mg n = 66 | Placebo n = 47 | 100 mg n = 46 | Placebo n = 618 | Unit Dose* n = 602 |
| Patients with pain relief (grade 0/1) | 38% | 71% | 19% | 78% | — | — |
| Patients with no pain | 15% | 52% | 11% | 41% | — | — |
| Results at 6 hours | | | | | | |
| Patients with pain relief | — | — | — | — | 52% | 79% |
| Patients with no pain | — | — | — | — | 23% | 51% |

*Unit dose: 2 tablets: 500 mg APAP/500 mg ASA/130 mg CAF.

As can be observed from the results presented in Table 5, at 2 hours, the percent pain relief efficacy of sumatriptan Imitrex®, 100 mg) is similar to the pain relief efficacy afforded by a unit dose of the APAP/ASA/CAF combination treatment of the present invention (sumatriptan: 56%/57% versus APAP/ASA/CAF: 59%). At 2 hours, the percentage of subjects experiencing no pain after sumatriptan dosing was 23%/24%, while the percentage of subjects experiencing no pain after APAP/ASA/CAF dosing was 21%. Similarly, at 4 hours postdose of sumatriptan and at 6 hours postdose of the APAP/ASA/CAF combination treatment of the present invention, the percentage of subjects experiencing pain relief was 71%/78% with sumatriptan and 79% with the APAP/ASA/CAF combination treatment. At 4 hours postdose of sumatriptan and 6 hours postdose of the APAP/ASA/CAF combination of the present invention, the percentage of subjects experiencing no pain was 52%/41% with sumatriptan and 51% with the APAP/ASA/CAF combination treatment.

Thus, the unit dose of APAP/ASA/CAF combination treatment of the present invention is similar to a 100 mg single dose of sumatriptan in effectiveness for migraine pain relief and pain elimination. In addition, the ability of the APAP/ASA/CAF combination treatment to reduce or eliminate migraine pain was effective up to 6 hours postdose versus 4 hours for sumatriptam, based on the results of the studies presented herein and those of the published PDR Imitrex® studies.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims, be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

REFERENCES

1. Stewart W F, Lipton R B, Celentano D D, Reed M L. Prevalence of migraine headache in the United States; relation to age, income, race, and other sociodemographic factors. *JAMA* 1992;267:64–69.
2. Rasmussen B K, Breslau N. Migraine: Epidemiology. In: Olesen J, Tfelt-Hansen P, Welch K M A, eds. *The Headaches.* New York, N.Y.: Raven Press; 1993:Chptr. 22:169–173.
3. Stewart W f, Schecter A, Lipton R B. Migraine heterogeneity: disability, pain intensity, and attack frequence and duration. *Neurology.* 1994;44(suppl4):S24–S39.
4. Lipton R B, Stewart W F. Migraine in the United States: A review of epidemiology and health care use. *Neurology.* 1993:43(suppl3):S6–S10.
5. Edmeads J, Findlay H, Tugwell P, Pryse-Phillips W, Nelson R F, Murray T J. Impact for migraine and tension-type headache on lifestyle, consulting behavior and medication use: a Canadian population survey. *Can J. Neurol Sci.* 1993;20:131–137.
6. Lipton R B, Stewart W F. Medical consultation for migraine [abstract], *Neurology.* 1994;44(suppl2):199.
7. Rasmussen B K, Jensen R, Olesen J. Impact of migraine on sickness, absence and utilization of medical services: a Danish population study. *J Epidemiol Community Health.* 1992;46:443–446
8. Micieli G. Suffering in silence. In: Edmeads J. Editor. *Migraine: a brighter future.* Worthing: Cambridge Medical Publications. 1993:1–7.
9. Lipton R B, Stewart W F, Celentano D D, Reed M L. Undiagnosed migraine: A comparison of symptom-based and physician diagnosis. *Arch Int Med.* 1992;152:1273–1278.
10. Celentano D D, Stewart W F, Lipton R B, Reed M L. Medication use and disability among migraineurs: a national probability sample survey. *Headache.* 1992;32:223–228.
11. Stang P E, Osterhaus J T, Celentano D D. Migraine: patterns of healthcare use. *Neurology.* 1994;44(Suppl 4):S47–S55.
12. Gilkey S J, Ramadan N M. Use of over-the-counter drugs in migraine. *CNS Drugs.* 1996;Aug 6(2):83–88.
13. Lipton R B, Newman L C, Solomon S. Over-the-counter medication and the treatment of migraine. *Headache.* 1994;34:547–548.
14. Lipton R b, Solomon S, Sheftell F D. Medical consultation for migraine: Results of the AASH Gallup Survey. *Headache.* 535–563, 1995.

15. Migliardi J R, Armellino J J, Friedman M, Gillings D B, B6eaver W T. Caffeine as an analgesic adjuvant in tension headache. *Clin Pharmacol Ther.* 1994;56:576–586.

16. Laska E M, Sunshine A, Mueller F, Elvers W B, Siegel C, Rubin A. Caffeine as an analgesic adjuvant. *JAMA* 1984;251:1711–1718.

17. Olesen J. A review of current drugs for migraine. *J. Neurology.* 1991; 238(suppl 1):S23–S27.

18. Solomon G D. Therapeutic advances in migraine. *J Clin Pharmacol.* 1993;33:200–209.

19. Stewart W F, Lipton R B, Population-based clinical trials in headache. Olesen J, Tfelt-Hansen, P, eds. *Headache Treatment: Trials Methodology and New Drugs,* New York, N.Y.: Raven Press; 1997:65–70.

20. Headache Classification Committee of the International Headache Society. Classification and diagnostic criteria for headache disorders, cranial neuralgias and facial pain. *Cephalalgia.* 1988;8(suppl 7): 1928.

What is claimed is:

1. A method for treating migraine pain and the cluster of symptoms characteristic of a migraine attack, the symptoms selected from the group consisting of nausea, photophobia, phonophobia and functional disability, comprising administering to a human subject a composition comprising a combination of acetaminophen, aspirin and caffeine in an amount effective to reduce or eliminate the migraine pain and one or more of said symptoms characteristic of migraine.

2. The method according to claim 1, wherein two or more of said symptoms characteristic of migraine are reduced or eliminated.

3. The method according to claim 1, wherein said composition is administered in a solid oral dosage form.

4. The method according to claim 3, wherein said dosage form is selected from the group consisting of tablets, pills, caplets and capsules.

5. The method according to claim 1, wherein said composition is administered as a suppository.

6. The method according to claim 4, wherein a single tablet, pill or capsule of said solid dosage form comprises acetaminophen in an amount of from about 200 to about 300 mg; aspirin in an amount of from about 200 to about 300 mg; and caffeine in an amount of about 55 to about 100 mg.

7. The method according to claim 5, wherein said composition comprises acetaminophen in an amount of 250 mg; aspirin in an amount of 250 mg; and caffeine in an amount of 65 mg.

8. The method according to claim 5, wherein two tablets, pills or capsules are administered to the human host about every four to six hours.

9. The method according to claim 7, wherein said composition is not readministered to said subject more frequently than once every six hours.

10. The method according to claim 1, wherein the amount of composition administered is effective to reduce or eliminate the migraine pain and two or more of said symptoms characteristic of migraine.

11. The method according to claim 1, wherein the amount of composition administered is effective to reduce or eliminate the migraine pain and three or more of said symptoms characteristic of migraine.

12. The method according to claim 1, wherein the amount of composition administered is effective to reduce or eliminate the migraine pain and all four of said symptoms characteristic of migraine.

13. A method of aborting a migraine attack, wherein the migraine attack is characterized by any one of the symptoms selected from the group consisting of nausea, photophobia, phonophobia and functional disability, comprising administering to a human subject during the prodrome phase of the migraine attack a migraine abortive effective amount of a composition comprising a combination of acetaminophen, aspirin and caffeine.

14. A method for treating migraine pain and nausea characteristic of a migraine attack comprising administering to a human subject a composition comprising a combination of acetaminophen, aspirin, and caffeine in an amount effective to reduce or eliminate the migraine pain and nausea characteristic of a migraine attack.

15. A method for treating migraine pain and photophobia characteristic of a migraine attack comprising administering to a human subject a composition comprising a combination of acetaminophen, aspirin, and caffeine in an amount effective to reduce or eliminate the migraine pain and photophobia characteristic of a migraine attack.

16. A method for treating migraine pain and phonophobia characteristic of a migraine attack comprising administering to a human subject a composition comprising a combination of acetaminophen, aspirin, and caffeine in an amount effective to reduce or eliminate the migraine pain and phonophobia characteristic of a migraine attack.

17. A method for treating migraine pain and functional disability characteristic of a migraine attack comprising administering to a human subject a composition comprising a combination of acetaminophen, aspirin, and caffeine in an amount effective to reduce or eliminate the migraine pain and functional disability characteristic of a migraine attack.

* * * * *